(12) United States Patent
Lee (10) Patent No.: US 8,316,855 B2
(45) Date of Patent: Nov. 27, 2012

(54) MEDITATION PILLOW USING CRANIOSACRAL THERAPY

(75) Inventor: Young-Jun Lee, Cheonan-si (KR)

(73) Assignee: Jinbiotech Co., Ltd, Cheonan (KR)

( * ) Notice: Subject to any disclaimer, the term of this patent is extended or adjusted under 35 U.S.C. 154(b) by 243 days.

(21) Appl. No.: 12/423,766

(22) Filed: Apr. 14, 2009

(65) Prior Publication Data

US 2009/0293885 A1 Dec. 3, 2009

(30) Foreign Application Priority Data

May 30, 2008 (KR) .................. 10-2008-0050540
Feb. 11, 2009 (KR) .................. 10-2009-0010860

(51) Int. Cl.
*A61G 15/00* (2006.01)

(52) U.S. Cl. ............ 128/845; 606/204; 606/240; 5/630; 5/636; 5/652; 602/17

(58) Field of Classification Search ............ 128/845, 128/870–871, 848; 606/4, 204, 240; 601/49, 601/51, 134; 5/621–624, 636–637, 640–641, 5/652, 657; 602/17, 18
See application file for complete search history.

(56) References Cited

U.S. PATENT DOCUMENTS

| | | | | | |
|---|---|---|---|---|---|
| 3,981,032 | A | * | 9/1976 | Brooks | 5/639 |
| 4,850,067 | A | * | 7/1989 | Latorre | 5/636 |
| 5,070,865 | A | * | 12/1991 | Iams | 606/240 |
| 5,267,931 | A | * | 12/1993 | Faetini | 482/140 |
| 5,581,831 | A | * | 12/1996 | Xiang | 5/636 |
| 5,820,573 | A | * | 10/1998 | Ramos | 601/134 |
| 7,020,919 | B2 | * | 4/2006 | Inaba | 5/638 |
| 7,331,631 | B1 | * | 2/2008 | Yeh | 297/391 |
| 8,161,588 | B1 | * | 4/2012 | Anson | 5/636 |
| 2004/0158176 | A1 | * | 8/2004 | Park | 601/18 |
| 2009/0131973 | A1 | * | 5/2009 | Zacharias | 606/204 |
| 2009/0241967 | A1 | * | 10/2009 | Orencel | 128/845 |
| 2012/0024295 | A1 | * | 2/2012 | Mihin | 128/845 |

* cited by examiner

*Primary Examiner* — Nicholas Lucchesi
*Assistant Examiner* — Kari Petrik (57) ABSTRACT

A meditation pillow using craniosacral therapy is disclosed. The meditation pillow includes a columna vertebralis supporting part formed in a user's neck direction to support a part of a columna vertebralis located thereon, an occipital region supporting part formed at a rear of the columna vertebralis supporting part to support an occipital region of a head located thereon, and an occipital region acupressure part protrudingly formed along a superior nuchal line between an atlas and an occipital bone to stimulate nerve fibers of the occipital region.

11 Claims, 9 Drawing Sheets

MEDITATION PILLOW USING CRANIOSACRAL THERAPY

BACKGROUND OF THE INVENTION

The present invention relates to a meditation pillow using craniosacral therapy, and more particularly, to a meditation pillow using craniosacral therapy to relax a tensed muscle group of an occipital region and, as a result, to relax a dura mater system of a craniosacral region by stimulating the occipital region using a weight of a user's head.

Many researches have reported that a human brain, skull and sacrum (in the pelvic region) when moved minutely, causes cerebrospinal fluid to flow along a brain and a spinal cord. While circulating through a spinal canal and a skull as blood flows through blood vessels, cerebrospinal fluid contacts with a nervous system, a musculoskeletal system, a vascular system, a lymphatic system, an endocrine system, a respiratory system, and so on, and thereby controls and integrates the organ systems of the human body.

Tension and repetitive stresses applied to a human body affect a central nervous system, and interrupt normal circulation of cerebrospinal fluid, which causes problems to organs associated with a nervous system, a musculoskeletal system, a vascular system, a lymphatic system, an endocrine system, and a respiratory system.

Craniosacral therapy (CST) is a manual treatment approach that improves a central nervous system and circulation of cerebrospinal fluid through manual contact and stimulating a craniosacral region through minute manual pressure.

Conventional medical treatment by CST depends on only a therapist's manual treatment. However, there is a proficiency difference between each physical therapist, and a patient's condition may become worse due to a physical therapist's error of judgment or poor treatment.

Further, if there is a high demand for a therapist, a patient could wait a long time for an appointment, and receive a short or rushed treatment from that therapist. Thus, such a treatment has little effect, and requires a long wait time.

SUMMARY OF THE INVENTION

Therefore, the present invention relates to a meditation pillow using craniosacral therapy to normalize a central nervous system and circulation of cerebrospinal fluid by stimulating a craniosacral region while a user lies down.

The present invention also relates to a meditation pillow (using craniosacral therapy) including an occipital region acupressure part to stimulate nerve fibers between an atlas and a skull at an area on which an occipital region is located, thereby relaxing associated muscles and promoting circulation of cerebrospinal fluid.

The present invention further relates to a meditation pillow (using craniosacral therapy) including an occipital bone acupressure part to stimulate an occipital bone, thereby exerting influence on autonomic nerve control of respiration, relaxing a tensed sympathetic nervous system, and activating circulation of cerebrospinal fluid.

Additional objects and/or advantages of the invention will be set forth in part in the description which follows and, in part, will be obvious from the description, or may be learned by practice of the invention.

To achieve these objects and other advantages and in accordance with the purpose of the invention, as embodied and broadly described herein, a meditation pillow using craniosacral therapy includes: a columna vertebralis supporting part formed in a user's neck direction to support a part of a columna vertebralis located thereon; an occipital region supporting part formed at a rear of the columna vertebralis supporting part to support an occipital region of a head located thereon; and an occipital region acupressure part protrudingly formed along a superior nuchal line between an atlas and an occipital bone to stimulate nerve fibers of the occipital region.

In accordance with another aspect of the invention, a meditation pillow using craniosacral therapy includes: a columna vertebralis supporting part formed in a neck direction to support a columna vertebralis located thereon; an occipital region supporting part formed at a rear of the columna vertebralis supporting part to support an occipital region of a head located thereon; a neck supporting part formed at both side surfaces of the columna vertebralis supporting part to support the neck; and an occipital bone acupressure part formed at a top of the neck supporting part to stimulate an occipital bone of the head.

DETAILED DESCRIPTION OF THE EMBODIMENTS

Now, embodiments of the present invention will be described in detail with reference to the drawings.

Referring to FIGS. 1 to 6, a meditation pillow 100 using craniosacral therapy according to an embodiment of the present invention includes a columna vertebralis supporting part 110 on which a columna vertebralis is seated, an occipital region supporting part 120 on which an occipital region is seated, and an occipital region acupressure part 130 to stimulate nerve fibers of the occipital region. The meditation pillow 100 using craniosacral therapy may further include a neck supporting part 140 to support a neck, auxiliary supporting parts 150 to support the columna vertebralis supporting part 110, an occipital bone acupressure part 160 to stimulate an occipital bone, a scent generating part 180 to generate scent, a sound generating part 190 to generate sound, or one or more these.

The columna vertebralis supporting part 110 extends in a spinal direction (Y-axis direction) and is formed to have a predetermined height, so that an upper part of a user's columna vertebralis can be seated on the columna vertebralis supporting part 110 when the user lies down. The columna vertebralis supporting part 110 may be formed to have two or more heights. The columna vertebralis supporting part 110 may be formed in such a structure that the two or more heights are decreased in sequence, so as to maintain a normal curve of the columna vertebralis. Also, as shown in FIG. 3, a surface of the columna vertebralis supporting part 110 may be formed to have a concave surface, so that a load (according to the weight of a head and upper part of a body) can be concentrated on the columna vertebralis.

Figure 1:
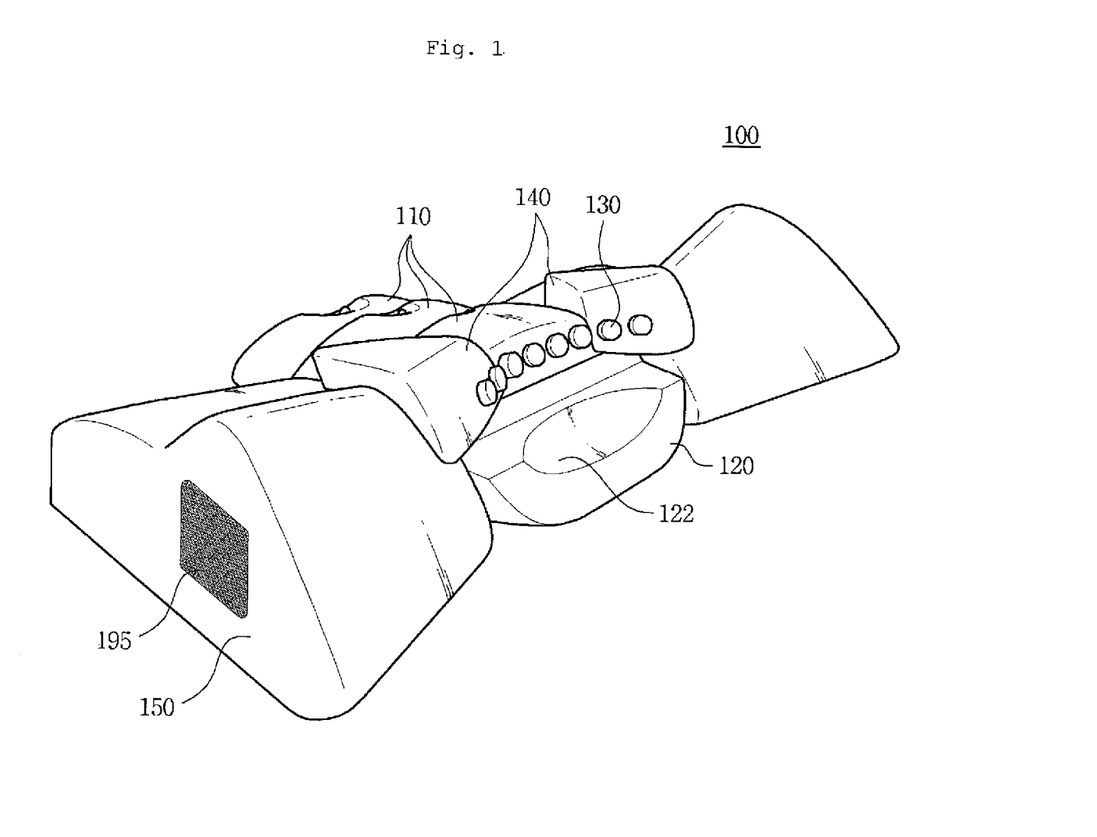
FIG. 1 is a perspective view of a meditation pillow using craniosacral therapy according to an embodiment of the present invention.
Figure 2:
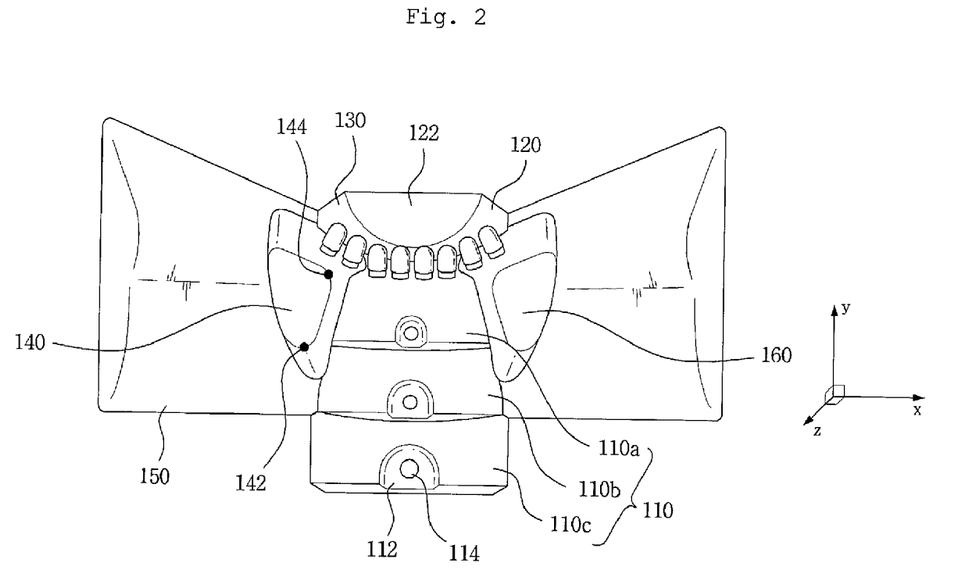
FIG. 2 is a plan view of the meditation pillow using craniosacral therapy according to an embodiment of the present invention.
Figure 3:
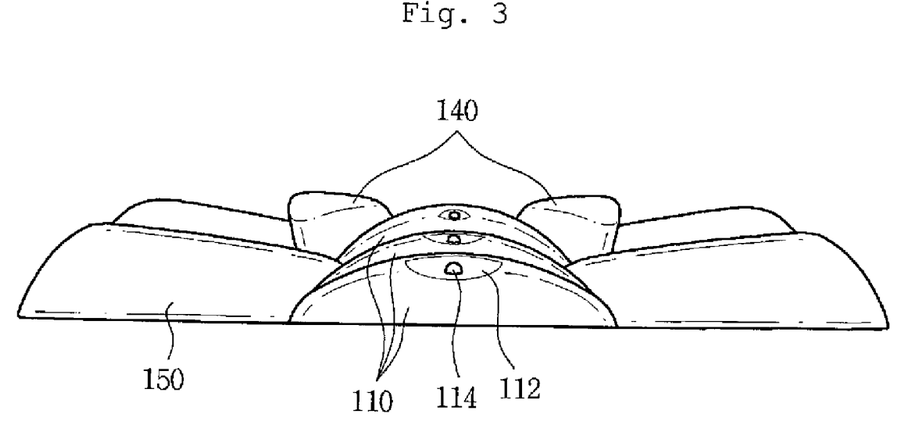
FIG. 3 is a front view of the meditation pillow using craniosacral therapy according to an embodiment of the present invention.
Figure 4:
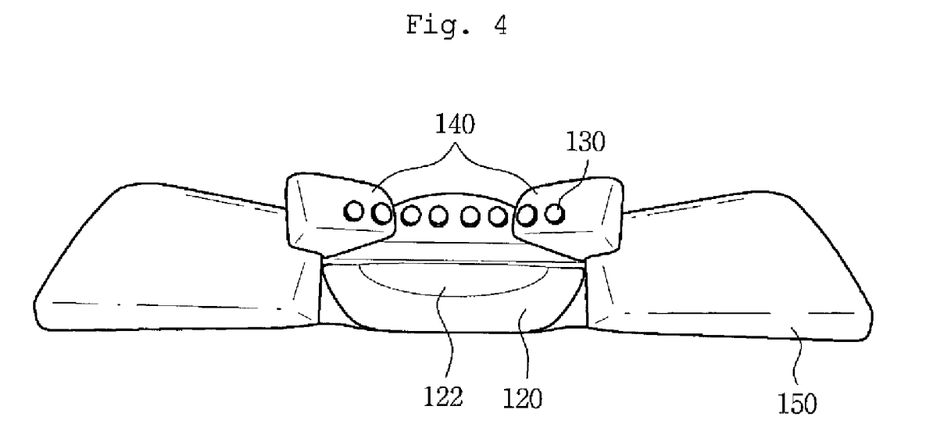
FIG. 4 is a rear view of the meditation pillow using craniosacral therapy according to an embodiment of the present invention.
Figure 5:
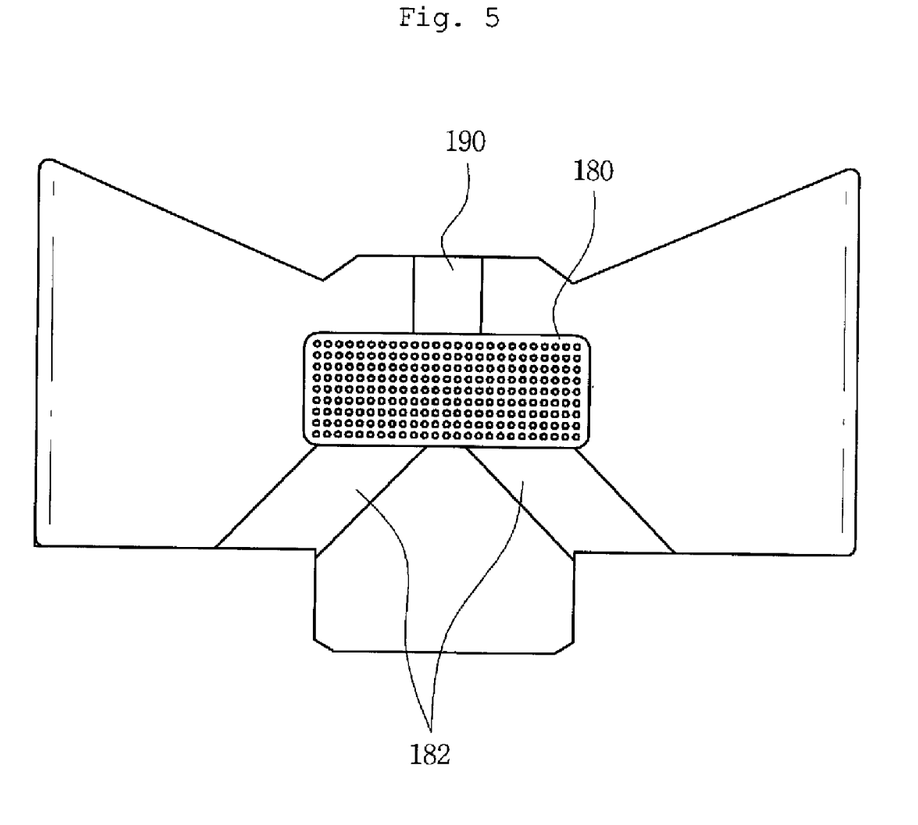
FIG. 5 is a bottom view of the meditation pillow using craniosacral therapy according to an embodiment of the present invention.

As shown in FIGS. 2 and 3, the columna vertebralis supporting part 110 includes a first columna vertebralis supporting part 110a, a second columna vertebralis supporting part 110b, and a third columna vertebralis supporting part 110c, which have different heights from each other. Although it has been described in this embodiment that the columna vertebralis supporting part 110 is divided into three sections, the number of the divided sections and the height difference between the divided sections are not limited thereto, and can be changed diversely.

The first columna vertebralis supporting part 110a is formed to be located at the uppermost position of the spine and to have the highest height. In order to satisfy a physiological curve of the columna vertebralis, the first columna vertebralis supporting part 110a may be formed to have a height of 5 to 10 cm, preferably, 7 to 8 cm. The second columna vertebralis supporting part 110b extends from the first columna vertebralis supporting part 110a, and has a height lower than the first columna vertebralis supporting part 110a. The third columna vertebralis supporting part 110c extends from the second columna vertebralis supporting part 110b, and has a height lower than the second columna vertebralis supporting part 110b. In other words, the heights of the first to third columna vertebralis supporting parts 110a to 110c are decreased in order from the first columna vertebralis supporting part 110a to the third columna vertebralis supporting part 110c. Accordingly, a load (according to the weight of a head and an upper part of a body) is concentrated on the columna vertebralis, and tensed muscles around the columna vertebralis are relaxed. As a result, the normal curve of the columna vertebralis can be maintained, and the columna vertebralis can be healed.

The columna vertebralis supporting part 110 may be formed with a columna vertebralis receiving recess 112, in which the columna vertebralis can be comfortably positioned. The columna vertebralis receiving recess 112 may be provided with a columna vertebralis acupressure protrusion 114 therein to obtain an acupressure effect by stimulating the columna vertebralis.

In order to prevent the columna vertebralis from being excessively pressed by a weight of an upper part of a body and a height difference of the columna vertebralis supporting part, the columna vertebralis receiving recess 112 may be formed at an area of the columna vertebralis supporting part 110 in which the height difference is created. In a case where the columna vertebralis supporting part 110 includes the first to third columna vertebralis supporting parts 110a to 110c as described above, the columna vertebralis receiving recess may be formed at each of the first to third columna vertebralis supporting parts.

So as to obtain an acupressure effect by stimulating the columna vertebralis seated in the columna vertebralis receiving recess 112, the columna vertebralis acupressure protrusion 114 may be formed to have a predetermined height in the columna vertebralis receiving recess 112.

The occipital region supporting part 120 is provided at the rear of the columna vertebralis supporting part 110, so that an occipital region of a head can be located thereon. In order not to only prevent the head from touching the ground but also allow the weight of the head to be exerted downward, the occipital region supporting part 120 is formed to have a height lower than the first columna vertebralis supporting part 110a. Also, in order to prevent the occipital region from being excessively pressed by the weight of the head, the occipital region supporting part 120 may be formed with an occipital region receiving recess 122 having a curved surface similar to the occipital region.

The neck supporting part 140 is provided at both side surfaces of the columna vertebralis supporting part 110, so as to support a user's neck. A portion 142 of the neck supporting part 140 serves to support each side portion of the neck, and another portion 144 of the neck supporting part 140 serves to support each side portion of the head, so that the head can be securely supported.

The occipital region acupressure part 130 is formed at the rear of the columna vertebralis supporting part 110, in order to stimulate nerve fibers of the occipital region. Specifically, the occipital region acupressure part 130 may be protrudingly formed along a superior nuchal line between an atlas and an occipital bone, in order to stimulate an area between the atlas and the occipital bone of the occipital region. The occipital region acupressure part 130 stimulates fourteen nerve fibers located at the left and right sides of the occipital region by a load due to the weight of the head. Therefore, relaxation and traction of the associated muscles are achieved, the columna vertebralis is set to a beneficial position, and blood to the brain and cerebrospinal fluid can be smoothly supplied. As a result, brain activity is increased, and a pain in the head or neck is reduced.

In order to increase the acupressure effect for the nerve fibers of the occipital region, the occipital region acupressure part 130 may include one or more acupressure bars. Also, in order to increase the acupressure effect for the superior nuchal line between the atlas and the occipital bone, eight acupressure bars may be included, just like a manual treatment using four fingers in each of the left and right hands. In a case where the neck supporting part 140 is not included, two to eight acupressure bars may be located at the rear of the columna vertebralis supporting part 110. In a case where the neck supporting part 140 is included, the acupressure bars may be formed at the rear of the columna vertebralis supporting part 110 and the neck supporting part 140.

The height (i.e., length in axial direction) of each occipital region acupressure part 130 may be formed adjustable so as to conform to differing occipital regions of each user and to adjust stimulus intensity. For instance, the acupressure bar of the occipital region acupressure part 130 may be formed in a screw thread shape, so as to move up and down by action of the screw thread.

Also, the acupressure bar of the occipital region acupressure part 130 may be connected to a vibration motor, so as to move up and down (i.e., axial direction of the occipital region acupressure part 130) by action of the vibration motor. In such a case, the occipital region acupressure part 130 can be applied to differing occipital region shapes, and can adjust stimulus intensity. Further, the number and time of the up/down movement of the acupressure bar can be adjusted. Accordingly, the acupressure effect can be increased.

The occipital region acupressure part 130 may be made of a material having a predetermined hardness, such as silicon, polyurethane, etc., to secure a high acupressure effect. The occipital region acupressure part 130 may further include a cover made of a rubber material or the like to prevent excessive stimulus.

Also, the occipital region acupressure part 130 may be made of a material to help transmit far infrared rays, such as jade, tote marine, etc., to increase the amount of far infrared rays absorbed in the body. The occipital region acupressure part 130 may contain a light source (e.g., light emitting diode) thereinside to radiate light at a certain wavelength (e.g., far infrared).

Figure 6:
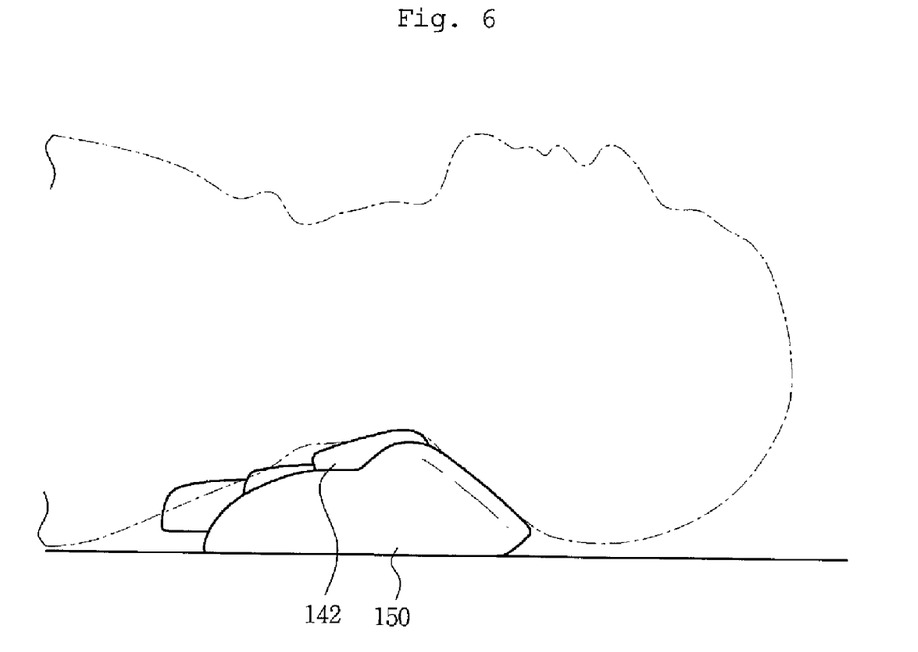
FIG. 6 is a view showing a used state of the meditation pillow using craniosacral therapy according to an embodiment of the present invention.

As shown in FIG. 6, while a user lies down, the user's head and neck are supported by the neck supporting part 140, and the user's occipital region is located on the occipital region acupressure part 130.

The auxiliary supporting parts 150 are provided at both side surfaces of the columna vertebralis supporting part 110, and extend in a direction (X-axis direction) perpendicular to the columna vertebralis supporting part 110, so as to serve to support the columna vertebralis supporting part 110. The auxiliary supporting parts 150 may be formed to have two-stage heights so that the user's head can be comfortably located thereon, or may be formed in the same shape as an already-known pillow so that the user can use the meditation pillow of the present invention as a general pillow. The auxiliary supporting parts 150 are not limited in length. Although it has been described that the two auxiliary supporting parts 150 are provided at both the side surfaces of the columna vertebralis supporting part 110, only a single auxiliary supporting part may be provided at one side surface of the columna vertebralis supporting part 110.

The scent generating part 180 contains a scent generating material to create a scent effect, such as herbs or the like. The scent from the scent generating part 180 is evenly spread through scent channels 182. The scent generating part 180 may be provided at a bottom of the meditation pillow. The scent generating material may include herbs, such as ligusticum chuanxiong, angelica gigantis radix, angelica dahurica root, magnolia kobus, asarum forbesii maxim, atractylodes macrocephala koidz, angelica tenuissima, paeonia suffruticosa, etc.

The sound generating part 190 includes a sound instrument to generate sound useful for sleep. The sound instrument may be provided at the bottom of the meditation pillow. A speaker 195 may be provided at the side or top of the meditation pillow.

Figure 7:
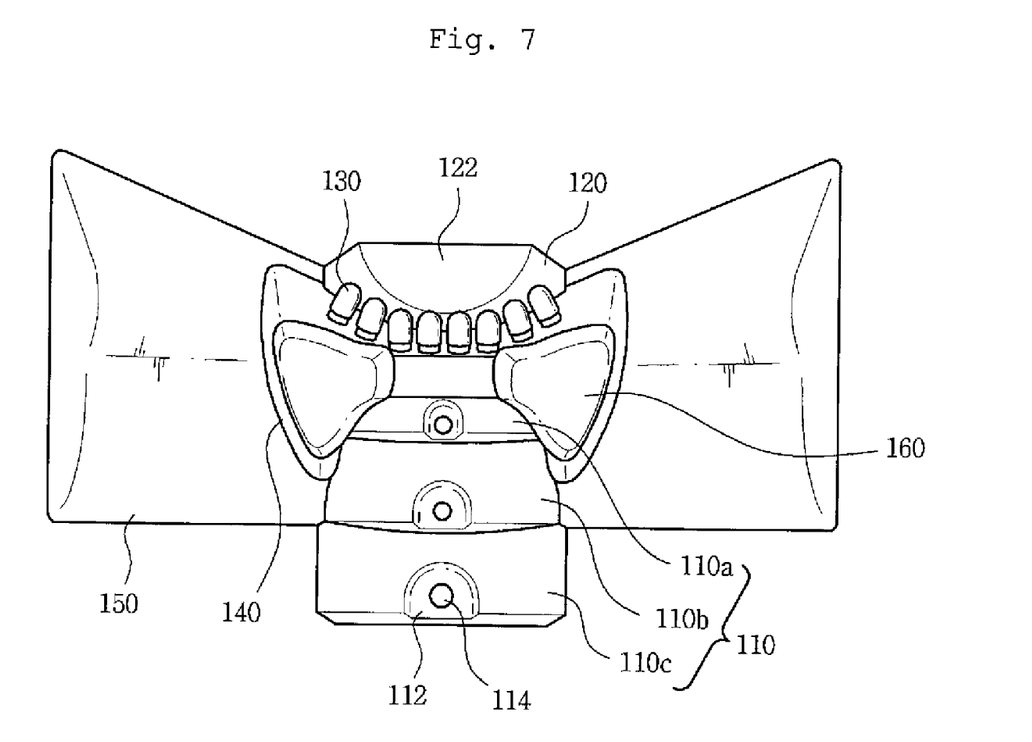
FIG. 7 is a plan view of a meditation pillow using craniosacral therapy according to another embodiment of the present invention.
Figure 8:
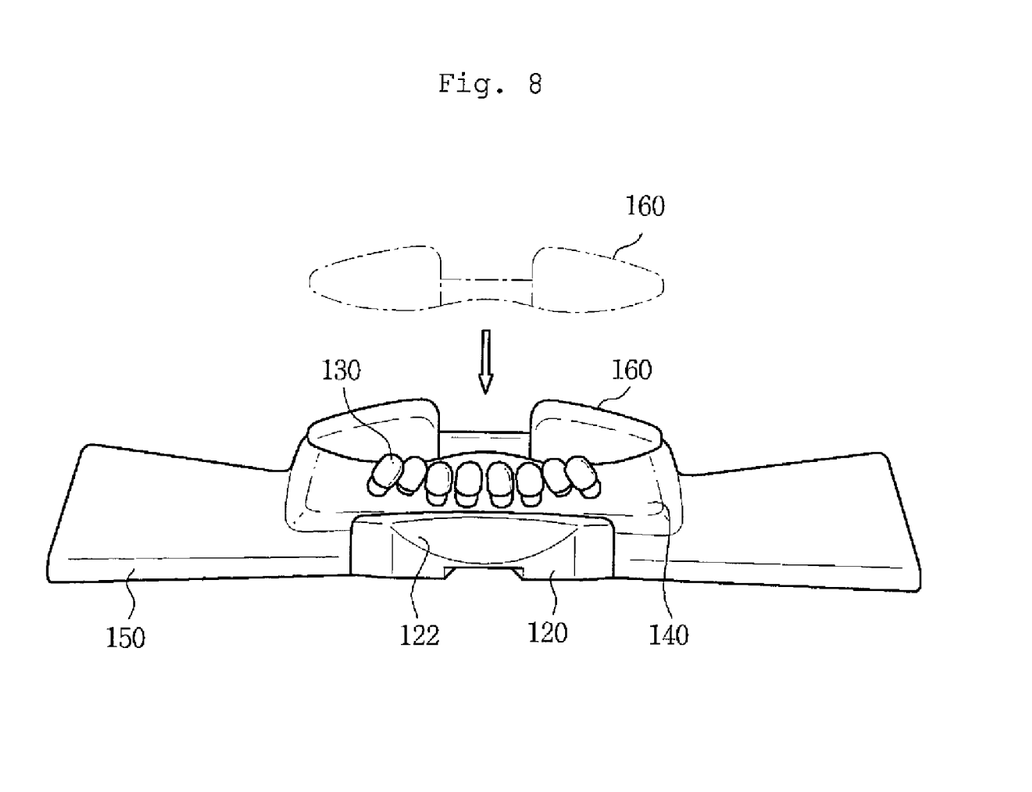
FIG. 8 is a rear view of the meditation pillow using craniosacral therapy according to another embodiment of the present invention.
Figure 9:
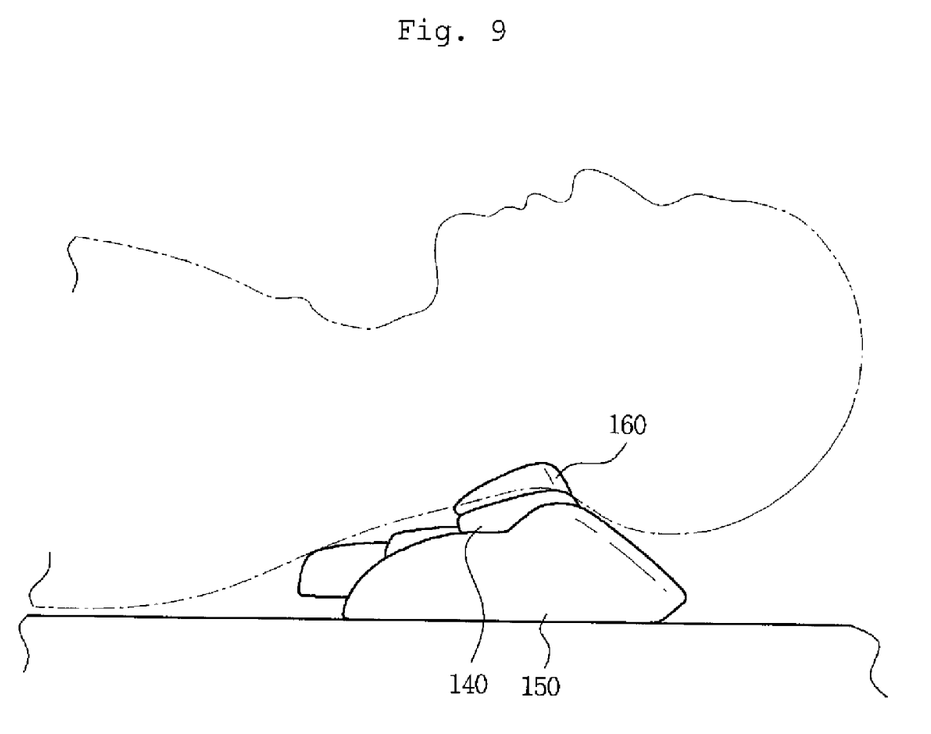
FIG. 9 is a view showing a used state of the meditation pillow using craniosacral therapy according to another embodiment of the present invention.

FIG. 7 is a plan view of a meditation pillow using craniosacral therapy according to another embodiment of the present invention. FIG. 8 is a rear view of the meditation pillow using craniosacral therapy according to another embodiment of the present invention. FIG. 9 is a view showing a used state of the meditation pillow using craniosacral therapy according to another embodiment of the present invention.

Referring to FIGS. 7 to 9, a meditation pillow according to another embodiment of the present invention includes an occipital bone acupressure part 160 to stimulate an occipital bone. The occipital bone acupressure part 160 is provided on the neck supporting part, and is protrudingly formed in a head direction (Z-axis direction).

The occipital bone acupressure part 160 to stimulate the occipital bone may be provided at a position on which a lower part of a mastoid process of the occipital bone is located, or may be provided at a position on which a fourth ventricle of the occipital bone is located. In order to increase the acupressure effect, the occipital bone acupressure part 160 may be provided with an occipital bone acupressure bar at an end portion thereof. In a case where the occipital bone acupressure part is disposed at a position on which a lower part of the mastoid process is located, the position of the head is not needed to move. However, in a case where the occipital bone acupressure part is disposed at a position on which the fourth ventricle is located, as shown in FIG. 9, the position of the head needs to be adjusted so that the occipital bone acupressure part 160 is located at a position corresponding to the fourth ventricle.

The occipital bone acupressure part 160 may be formed so as to be removably coupled to the neck supporting part 140. A bottom of the occipital bone acupressure part 160 may have the same shape as a top of the neck supporting part 140 so that the occipital bone acupressure part 160 can be coupled to or removed from the neck supporting part 140.

The occipital bone acupressure part 160 serves to stimulate a lower part of the mastoid process or the fourth ventricle by a load due to the weight of the head, thereby exerting influence on diaphragm activity and autonomic nerve control of respiration. Accordingly, a tensed sympathetic nervous system is relaxed, cerebrospinal fluid is smoothly circulated, and thus a headache or a fever is alleviated.

The meditation pillow according to the present invention may be made of an elastic material for comfort and traction, such as sponge, polyurethane, memory foam, etc. The meditation pillow according to the present invention may be also made of a non-elastic material, such as wood, plastic, etc., in order to increase the acupressure effect.

As apparent from the above description, the meditation pillow using craniosacral therapy according to the present invention can relax tensed muscle groups of an occipital region associated with a head and a dura mater system of a craniosacral region by successively stimulating the occipital region while a user lies down. Accordingly, circulation of cerebrospinal fluid is promoted, and circulation of brain blood is improved. Brain development is promoted, and a curve in a columna vertebralis can be set to a beneficial position.

Further, relaxation and traction of associated muscles are achieved by naturally stimulating nerve fibers in the right and left sides of the occipital region by a weight of a users head, the dislocated columna vertebralis is set to a normal position, and brain blood and cerebrospinal fluid can be smoothly supplied. As a result, brain activity is increased, and a pain in the head or neck is reduced.

Further, the meditation pillow stimulates an occipital bone by a load due to the weight of the users head, thereby exerting influence on diaphragm activity and autonomic nerve control of respiration. Accordingly, a tensed sympathetic nervous system is relaxed, cerebrospinal fluid is smoothly circulated, and thus a headache or a fever is alleviated.

Those skilled in the art will appreciate that the present invention may be carried out in other specific ways than those set forth herein without departing from the spirit and essential characteristics of the present invention.

The above embodiments are therefore to be construed in all aspects as illustrative and not restrictive. The scope of the invention should be determined by the appended claims and their legal equivalents, not by the above description, and all changes coming within the meaning and equivalency range of the appended claims are intended to be embraced therein.

What is claimed is:

1. A meditation pillow comprising:
   a columna vertebralis supporting part configured to support a part of a columna vertebralis;
   an occipital region supporting part disposed at a first side of the columna vertebralis supporting part and configured to support an occipital region of a head;
   a bottom portion configured to lie substantially planar to a surface;
   first and second neck supporting parts disposed on a second and third side of the columna vertebralis supporting part and comprising a top surface disposed above a top surface of the columna vertebralis supporting part, the neck supporting part being configured to support a neck;
   an occipital region acupressure part comprising at least one acupressure bar extending from a surface of the neck supporting part proximal to the occipital region supporting part and sloping towards the top of a head of a user when the head is located by the occipital region supporting part, and adapted to stimulate nerve fibers of the occipital region when the occipital region of the head locates the occipital region supporting part;
   and an occipital bone acupressure part configured to stimulate an occipital bone of the head,
   wherein the columna vertebralis supporting part includes a first columna vertebralis supporting part having a first height and a second columna vertebralis supporting part having a second height lower than the first height.

2. The meditation pillow of claim 1, wherein the columna vertebralis supporting part includes at least one columna vertebralis receiving recess configured to support a user's columna vertebralis so that the user's columna vertebralis is comfortably mounted thereon.

3. The meditation pillow of claim 1, wherein the columna vertebralis supporting part includes at least one columna vertebralis acupressure protrusion configured to stimulate a user's columna vertebralis mounted thereon.

4. The meditation pillow of claim 1, wherein the columna vertebralis supporting part further includes a third columna vertebralis supporting part having a third height lower than the second height.

5. The meditation pillow of claim 1, wherein the occipital region supporting part includes an occipital region receiving recess to support the user's occipital region.

6. The meditation pillow of claim 1, wherein the occipital region acupressure part is configured to move up and down.

7. The meditation pillow of claim 1, wherein the occipital region acupressure part includes a lamp configured to radiate infrared rays or a laser beam.

8. The meditation pillow of claim 1, the meditation pillow further comprising:
   an auxiliary supporting part disposed at the second or third side of the columna vertebralis supporting part and configured to support the columna vertebralis supporting part.

9. The meditation pillow of claim 1, the meditation pillow further comprising:
   a scent generating part configured to generate scent.

10. The meditation pillow of claim 1, the meditation pillow further comprising:
    a sound generating part configured to generate sound.

11. The meditation pillow of claim 1, wherein the at least one acupressure bar corresponds to a user's superior nuchal line between the user's atlas and the user's occipital bone and is adapted to stimulate the nerve fibers of the occipital region.

* * * * *